United States Patent

Hoehn

[11] 4,202,985
[45] May 13, 1980

[54] IMIDAZOLYLETHOXY DERIVATIVES OF QUINOLINE-3-METHANOLS

[75] Inventor: Hans Hoehn, Tegernheim, Fed. Rep. of Germany

[73] Assignee: E. R. Squibb & Sons, Inc., Princeton, N.J.

[21] Appl. No.: 954,728

[22] Filed: Oct. 25, 1978

[51] Int. Cl.² .................. C07D 401/12; C07D 215/12; A61K 31/465
[52] U.S. Cl. .................. 546/176; 546/153; 546/155; 546/177; 424/258
[58] Field of Search ............... 546/153, 155, 157, 176, 546/177; 424/258

[56] References Cited

U.S. PATENT DOCUMENTS 3,839,574  10/1974  Godefroi et al. ............... 424/273
4,131,608  12/1978  Zirngibl et al. ............... 260/307 D

OTHER PUBLICATIONS

Heeres et al., Current Abstracts of Chemistry, vol. 67, Issue 734, Abstract 264882 (1977).
Heeres et al., Current Abstracts of Chemistry, vol. 67, Issue 734, Abstract 264883 (1977).
Current Abstracts of Chemistry, vol. 63, Issue 675, Heeres et al., Abstract 249387 (1976).

Primary Examiner—Donald G. Daus
Assistant Examiner—Diana G. Rivers
Attorney, Agent, or Firm—Lawrence S. Levinson

[57] ABSTRACT

Imidazolylethoxy derivatives of quinoline-3-methanols having the general formula

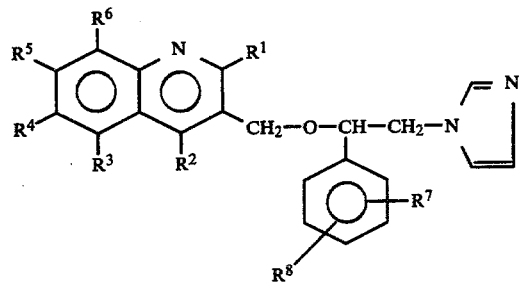

and their acid addition salts are useful as antifungal and antibacterial agents.

11 Claims, No Drawings

IMIDAZOLYLETHOXY DERIVATIVES OF QUINOLINE-3-METHANOLS

SUMMARY OF THE INVENTION

This invention relates to new 2-(1H-imidazol-1-yl)ethoxy derivatives of quinoline-3-methanols and the acid addition salts of these compounds. These new compounds have the general formula

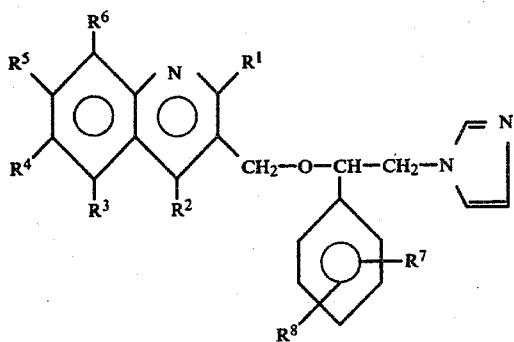

(I)

The symbols have the following meaning in formula I and throughout the specification:

$R^1$ to $R^8$ each is hydrogen, lower alkyl, hydroxy, lower alkoxy, lower alkylthio or halogen.

DETAILED DESCRIPTION OF THE INVENTION

The lower alkyl groups include straight or branched chain hydrocarbon groups containing 1 to 7 carbon atoms. Examples include methyl, ethyl, propyl, isopropyl, etc. The lower alkoxy and lower alkylthio groups include such lower alkyl groups bonded to an oxygen or sulfur, respectively, e.g., methoxy, ethoxy, propoxy, butoxy, t-butoxy, methylthio, ethylthio, propylthio, butylthio, isobutylthio, etc. In all of these the $C_1$-$C_4$, especially $C_1$-$C_2$, lower alkyl groups are preferred.

The halogens are the four common halogens, chlorine and bromine being preferred in that order. Preferably, but not necessarily, all halogens in a single compound are the same.

Preferred embodiments of this invention are compounds of formula I wherein $R^1$ to $R^8$ is hydrogen, lower alkyl of 1 to 4 carbons or halogen.

The most preferred embodiments are compounds of formula I wherein $R^1$, $R^3$ and $R^6$ each is hydrogen or halogen, especially hydrogen; $R^2$, $R^4$, $R^5$ and $R^8$ each is hydrogen, halogen, most especially halogen, particularly chlorine, and $R^7$ and $R^8$ are attached in the 2- and 4-positions of the phenyl ring, respectively.

The new compounds of formula I are formed by the following series of reactions.

A quinoline-3-carboxylic acid ester of the formula

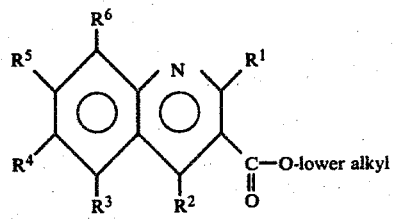

(II)

is reduced by means of a reducing agent, e.g. a metal hydride such as lithium aluminum hydride or sodium borohydride and the like to give the alcohol of the formula

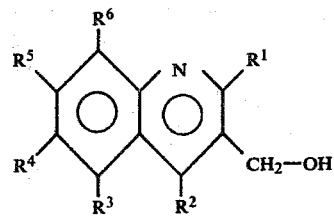

(III)

The alcohol of formula III is converted to the halomethyl derivative of the formula

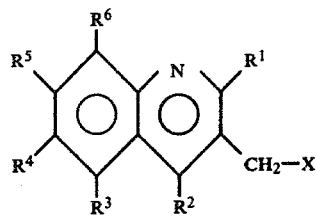

(IV)

wherein X represents a halogen, preferably chlorine, bromine or iodine, by means of an inorganic acid halide such as thionyl chloride, phosphorus oxybromide, etc.

The product of formula I is then prepared by reaction of the halo compound of formula IV with a substituted 1-(phenyl)-2-(1H-imidazol-1-yl)ethanol of the formula

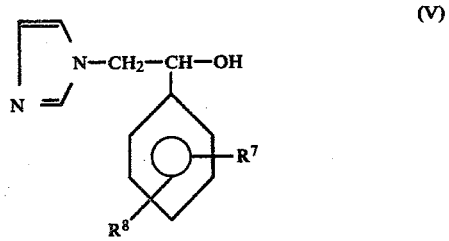

(V)

The inorganic acid formed during the reaction is neutralized by a base, e.g., alkali metal hydroxide, carbonate, amine, alcoholate or other similar bases known in the art.

The compounds of formula II, which are used as starting materials, are produced by the procedures described in Journal of Medicinal Chemistry, Vol. 20, 1001 (1977); ibid., Vol. 16 875 (1973) Tetrahedron Letters, 51, 4545 (1977), etc. The compounds of formula V, which are used as starting materials, are produced by the general methods described in Journal of Medicinal Chemistry, Vol. 12, 784 (1969).

The compounds of formula I form salts which are also part of this invention. The salts include acid-addition salts, particularly the non-toxic, physiologically acceptable members. The bases of formula I form salts by reaction with one or more equivalents of any of a variety of the common inorganic and organic acids providing acid addition salts including, for example, hydrohalides (especially hydrochloride and hydrobromide), sulfate, nitrate, borate, phosphate, oxalate, tartrate, maleate, citrate, acetate, ascorbate, succinate, benzenesulfonate, methanesulfonate, cyclohexanesulfamate and toluenesulfonate. The acid addition salts frequently provide a convenient means for isolating or purifying the product, e.g., by forming and precipitating a salt (which is not necessarily non-toxic) in an appropriate medium in which the salt is insoluble, then after separation of the salt, neutralizing with a base such as barium hydroxide or sodium hydroxide, to obtain the free base of formula I. Other salts may then be formed from the free base by reaction with one or more equivalents of acid containing the desired acid group.

The new compounds of formula I and their salts are useful as anti-fungal and anti-bacterial agents and may be used to combat infections in various mammalian species, such as mice, rats, dogs, guinea pigs and the like, particularly those due to organisms such as *Candida albicans*, as well as organisms such as *Trichomonas vaginalis* or *Trichophyton mentagrophytes*. For example, a compound or mixture of compounds of formula I or physiologically acceptable acid addition salt thereof can be administered orally to an infected animal, e.g., to a mouse, in an amount of about 5 to 25 mg. per kg. per day in 2 to 4 divided doses. These may be conventionally formulated in a tablet, capsule or elixir containing about 10 to 250 mg. per dosage unit, by compounding the active substance or substances with the conventional excipient, vehicle, binder, preservative, flavor, etc., as called for by accepted pharmaceutical practice. Preferably they are applied topically, e.g., intravaginally in a lotion or in a conventional cream base at a concentration of about 0.01 to 3 percent by weight for a period of about 3 to 7 days, two to four times daily.

The following examples are illustrative of the invention. Temperatures are on the Celsius scale.

EXAMPLE 1

4,6-Dichloro-3-[[1-(2,4-dichlorophenyl)-2-(1H-imidazol-1-yl)ethoxy]methyl]quinoline, hydrochloride (1:1)

(a) 4,6-Dichloroquinoline-3-carboxylic acid, ethyl ester

A mixture of 45.2 g. of 6-chloro-4-hydroxyquinoline-3-carboxylic acid, ethyl ester (0.18 mol.) and 250 ml. of thionyl chloride is refluxed for 20 hours. The excess thionyl chloride is then removed in vacuo, the residue treated with 200 ml. of water and the ester is extracted with ether. After washing the ethereal extract twice with water, it is dried with Na$_2$SO$_4$ and the solvent distilled off. The residual 4,6-dichloroquinoline-3-carboxylic acid, ethyl ester is triturated with petroleum ether (40°–60°), filtered and dried. Yield: 45.3 g. (93%); m.p. 87°–88°.

(b) 4,6-Dichloroquinoline-3-methanol 27 g. of 4,6-dichloroquinoline-5-carboxylic acid, ethyl ester (0.1 mol.) are dissolved in 600 ml. of anhydrous tetrahydrofuran. Nitrogen is passed through the flask and while stirring and cooling to 0°, 2.4 g. of lithium aluminum hydride are added a bit at a time in order to keep the reaction temperature at 0° to +5°. Stirring is continued for an additional five hours. Then 2.5 ml. of water, 2.0 ml. of aqueous sodium hydroxide (20%) and again 9 ml. of water are added. The precipitated inorganic salts are filtered off and the solvent is removed by a rotary evaporator. The resulting oil is dissolved in a small quantity of benzene and kept in the refrigerator. The crystallized 4,6-dichloroquinoline-3-methanol is filtered off and recrystallized from ethyl acetate; yield: 12.5 g. (55%); m.p 182°.

(c) 3-Chloromethyl-4,6-dichloroquinoline 11.4 g. of 4,6-dichloroquinoline-3-methanol (0.05 mol.) are added in portions to 150 ml. of thionyl chloride. The reaction mixture is allowed to stand for 24 hours at room temperature. Then the solution is filtered and the excess thionyl chloride removed by a rotary evaporator. The residue is triturated with water, filtered off, washed again with water and dried in a desiccator over P$_2$O$_5$ to obtain 3-chloromethyl-4,6-dichloroquinoline; yield: 11.5 g. (93.5%); m.p. 102°–105°. Recrystallization from cyclohexane does not change the melting point.

(d)
4,6-Dichloro-3-[[1-(2,4-dichlorophenyl)-2-(1H-imidazol-1-yl)ethoxy]methyl]quinoline, hydrochloride (1:1)

In a three necked flask, fitted with stirrer, reflux condenser and gas inlet tube are introduced 14.8 g. of sodium hydroxide (0.37 mol.) and 25 ml. of water. While passing nitrogen through the flask, the solution is cooled to 45° and then are added 3.85 g. of 1-(2,4-dichlorophenyl)-2-(1H-imidazol-1-yl)ethanol (0.015 mol.), [prepared according to J. Med. Chem., Vol. 12, 784 (1969)], 0.25 g. of benzyltrimethylammonium chloride and 25 ml. of tetrahydrofuran. To the mixture, which is warmed to 50°, a solution of 3.6 g. of 3-chloromethyl-4,6-dichloroquinoline (0.015 mol.) in 10 ml. of tetrahydrofuran is added from a prewarmed dropping funnel within 3 minutes. The mixture is stirred vigorously for 3 hours at 60° using a water bath. Then the warm mixture is transferred into a separating funnel, the lower aqueous sodium hydroxide is extracted with 10 ml. of tetrahydrofuran. The combined tetrahydrofuran layers are dried by means of sodium sulfate, and after the solvent has been removed, the residual oil is extracted with ether, treated with charcoal and filtered. To the solution of free base are added dropwise ethereal hydrochloric acid. The precipitated 4,6-dichloro-3-[[1-(2,4-dichlorophenyl-2-(1H-imidazol-1-yl)ethoxy]methyl]quinoline, hydrochloride is filtered off, dried in the vacuum desiccator and recrystallized from absolute ethanol; yield: 1.9 g. (25%); m.p. 148°–150°.

EXAMPLE 2

4,7-Dichloro-3-[[1-(2,4-dichlorophenyl)-2-(1H-imidazol-1-yl)ethoxy]methyl]quinoline, hydrochloride (1:2)

(a) 4,7-Dichloroquinoline-3-carboxylic acid, ethyl ester

A mixture of 30 g. of 7-chloro-4-hydroxyquinoline-3-carboxylic acid, ethyl ester, m.p. 299°–301°, (0.12 mol.) and 250 ml. of phosphorus oxychloride is refluxed for 4.5 hours. After removing the excess phosphorus oxychloride, the residue is triturated with water and dissolved in ether. The ethereal solution is washed with aqueous sodium carbonate (5%) and water, dried with sodium sulfate and the solvent is removed. The residual 4,7-dichloroquinoline-3-carboxylic acid, ethyl ester is triturated with petroleum ether (40°–60°), filtered off and dried; yield: 22 g. (68%); m.p. 81°–82°.

(b) 4,7-Dichloroquinoline-3-methanol

Following the procedure of Example 1b, 21 g. of 4,7-dichloroquinoline-3-carboxylic acid, ethyl ester (0.08 mol.) in 500 ml. of anhydrous tetrahydrofuran and 1.9 g. of lithium aluminum hydride yield 8.4 g. (46%) of 4,7-dichloroquinoline-3-methanol; m.p. 144°–145° (ethyl acetate).

(c) 3-Chloromethyl-4,7-dichloroquinoline 8 g. of 4,7-dichloroquinoline-3-methanol (0.035 mol.) and 100 ml. of thionyl chloride are reacted according to the procedure of Example 1c to obtain 7.1 g. (82.5%) of 3-chloromethyl-4,7-dichloroquinoline; m.p. 106°–107°.

(d) 4,7-Dichloro-3-[[1-(2,4-dichlorophenyl)-2-(1H-imidazol-1-yl)ethoxy]methyl]quinoline, hydrochloride (1:2)

5.2 g. of 1-(2,4-dichlorophenyl)-2-(1H-imidazol-1-yl)ethanol (0.02 mol.) dissolved in 45 ml. of anhydrous tetrahydrofuran and 0.8 g. of sodium hydride (55–60% dispersion in mineral oil) are stirred for 4.5 hours at room temperature. After the sodium salt formation is complete, 4.9 g. of 3-chloromethyl-4,7-dichloroquinoline (0.02 mol.) dissolved in 25 ml. of anhydrous tetrahydrofuran are added and the mixture is stirred at 50°–60° (bath temperature) for 4 hours. Then tetrahydrofuran is removed, the residue treated with water and extracted with ether. The ethereal layer is washed with water and dried with sodium sulfate. Addition of ethereal hydrochloric acid to the ether solution of the base precipitates the hydrochloride salt. For purification the hydrochloride is converted into the free base and again extracted and treated with ethereal hydrochloric acid. Recrystallization from ethyl acetate gives 2.1 g. (20%) of 4,7-dichloro-3-[[1-(2,4-dichlorophenyl)-2-(1H-imidazol-1-yl)ethoxy]methyl]quinoline, hydrochloride (1:2); m.p. 148°–149°.

The following additional products of formula C are obtained by the procedure of Example 1 by reacting the unsubstituted or substituted 1-phenyl-2-(1H-imidazol-1-yl)ethanol of formula A with the unsubstituted or substituted 3-chloromethylquinoline of formula B. The substituents apply to the respective formulas.

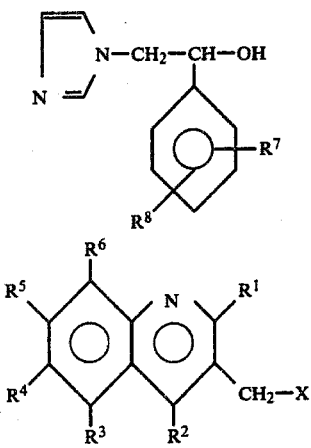

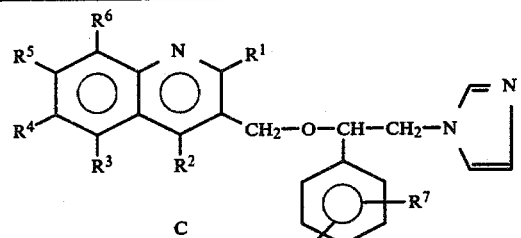

| Example | $R^1$ | $R^2$ | $R^3$ | $R^4$ | $R^5$ | $R^6$ | $R^7$ | $R^8$ |
|---|---|---|---|---|---|---|---|---|
| 3 | H | H | H | H | H | H | H | H |
| 4 | $CH_3$ | $CH_3$ | —OH | —OH | H | H | H | H |
| 5 | $C_2H_5$ | H | $-OC_2H_5$ | $-CH_3$ | H | H | 2-Cl | 4-Cl |
| 6 | $C_2H_5$ | $C_2H_5$ | $-OCH_3$ | $CH_3$ | H | H | H | 4-Cl |
| 7 | $C_2H_5$ | $CH_3$ | Br | H | H | H | H | 3-Br |
| 8 | $C_2H_5$ | $CH_3$ | H | H | H | H | 2-Br | 4-Br |
| 9 | $C_2H_5$ | H | Br | H | H | H | 3-Br | 4-Br |
| 10 | $C_2H_5$ | H | H | $CH_3$ | $-OCH_3$ | H | H | 4-Cl |
| 11 | $C_2H_5$ | H | Cl | $C_2H_5$ | —OH | H | H | 2-Cl |
| 12 | —OH | $CH_3$ | $-OC_2H_5$ | H | H | $-CH_3$ | 2-$CH_3$ | 4-$CH_3$ |
| 13 | $C_2H_5$ | $C_3H_7$ | Cl | H | H | H | H | 4-$OCH_3$ |
| 14 | $C_2H_5$ | H | Cl | $C_6H_5$ | H | H | H | 2-$OCH_3$ |
| 15 | $C_3H_7$ | H | —OH | H | H | H | H | 3-Cl |
| 16 | H | H | Cl | H | Cl | —OH | 2-Cl | 4-Cl |
| 17 | $CH_3$ | $CH_3$ | H | H | H | H | H | 4-Cl |
| 18 | H | H | Cl | H | H | H | H | H |
| 19 | Cl | H | Cl | H | H | H | 2-Cl | 4-Cl |
| 20 | Cl | $CH_3$ | Cl | H | H | H | 3-Cl | 4-Cl |
| 21 | $C_2H_5$ | —OH | Cl | H | H | H | ·H | 4-Cl |
| 22 | $C_2H_5$ | $CH_3$ | H | H | H | Cl | 2-Cl | 4-Cl |
| 23 | H | $-SCH_3$ | Cl | H | $C_2H_5$ | H | H | 4-Cl |
| 24 | H | $CH_3$ | Cl | H | H | $CH_3$ | H | 4-Cl |
| 25 | $-OC_2H_5$ | $CH_3$ | Br | H | H | H | H | 4-Cl |
| 26 | $-SC_2H_5$ | H | Cl | H | H | H | 2-Cl | 4-Cl |
| 27 | $C_2H_5$ | H | H | $-SCH_3$ | H | H | H | 4-Br |
| 28 | H | H | $-SCH_3$ | H | H | H | 2-Cl | 4-Cl |
| 29 | $-OC_2H_5$ | $CH_3$ | Cl | H | H | H | H | 4-Cl |
| 30 | $CH_3$ | H | $-SCH_3$ | H | H | H | H | 4-$SCH_3$ |
| 31 | $C_2H_5$ | H | I | H | H | H | H | 4-Cl |
| 32 | $C_2H_5$ | H | —OH | H | H | H | 3-OH | 5-OH |
| 33 | $C_2H_5$ | $CH_3$ | $-OC_4H_9$ | H | H | H | H | 4-Cl |

-continued

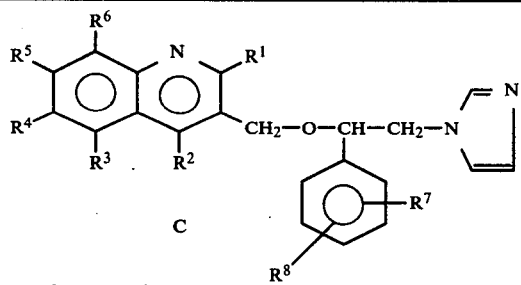

C

| Example | $R^1$ | $R^2$ | $R^3$ | $R^4$ | $R^5$ | $R^6$ | $R^7$ | $R^8$ |
|---|---|---|---|---|---|---|---|---|
| 34 | H | H | —$OC_3H_7$ | H | H | H | 2-Cl | 4-Cl |
| 35 | $C_2H_5$ | H | H | H | H | —$SCH_3$ | 2-Cl | 4-Cl |
| 36 | $C_2H_5$ | H | Cl | $CH_3$ | $CH_3$ | —OH | H | 4-Cl |

What is claimed is:

1. A compound of the formula

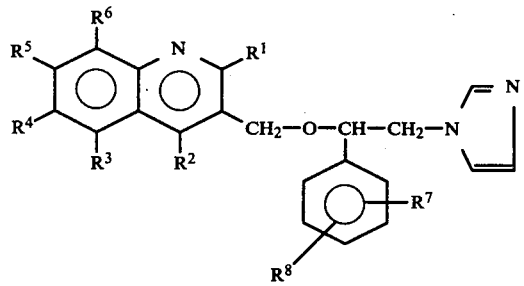

wherein $R^1$ to $R^8$ each is hydrogen, hydroxy, halogen, lower alkyl containing 1 to 7 carbons, lower alkoxy containing 1 to 7 carbons or lower alkylthio containing 1 to 7 carbons; and acid addition salts thereof.

2. A compound as in claim 1 wherein $R^4$ is halo.

3. A compound as in claim 1 wherein $R^5$ is halo.

4. A compound as in claim 1 wherein $R^7$ and $R^8$ each is halo.

5. A compound as in claim 4 wherein each halo is chloro.

6. A compound as in claim 1 wherein $R^7$ is 2-chloro and $R^8$ is 4-chloro.

7. A compound as in claim 1 wherein $R^1$ to $R^8$ each is hydrogen, halogen or $C_1$-$C_4$-lower alkyl.

8. A compound as in claim 1 wherein $R^1$ to $R^8$ each is hydrogen or halogen.

9. A compound as in claim 1 wherein $R^1$, $R^3$ and $R^6$ each is hydrogen; and $R^2$, $R^7$ and $R^8$ each is halogen; and acid addition salts thereof.

10. A compound as in claim 1 wherein $R^1$, $R^3$, $R^4$ and $R^6$ each is hydrogen; $R^2$ and $R^5$ each is chloro; $R^7$ is 2-chloro; and $R^8$ is 4-chloro.

11. A compound as in claim 1 wherein $R^1$, $R^3$, $R^5$ and $R^6$ each is hydrogen; $R^2$ and $R^4$ each is chloro; $R^7$ is 2-chloro; and $R^8$ is 4-chloro.

* * * * *